United States Patent
Subramanian et al.

(10) Patent No.: US 8,715,183 B2
(45) Date of Patent: May 6, 2014

(54) METHODS AND APPARATUS FOR AUTOMATED MEASURING OF THE INTERVENTRICULAR SEPTUM THICKNESS

(75) Inventors: Navneeth Subramanian, Bangalore (IN); Anand Magadi Narasimhamurthy, Bangalore (IN); Sheshadri Thiruvenkadam, Bangalore (IN); Dirk Ryan Padfield, Albany, NY (US)

(73) Assignee: General Electric Company, Niskayuna, NY (US)

( * ) Notice: Subject to any disclaimer, the term of this patent is extended or adjusted under 35 U.S.C. 154(b) by 652 days.

(21) Appl. No.: 12/825,755

(22) Filed: Jun. 29, 2010

(65) Prior Publication Data

US 2011/0319763 A1 Dec. 29, 2011

(51) Int. Cl.
A61B 8/00 (2006.01)

(52) U.S. Cl.
USPC ........... 600/437; 600/407; 600/443; 600/459; 382/128; 382/131

(58) Field of Classification Search
USPC ........................ 600/437, 443; 382/128, 131
See application file for complete search history.

(56) References Cited

U.S. PATENT DOCUMENTS

| | | | |
|---|---|---|---|
| 6,213,973 B1 * | 4/2001 | Eliasen et al. | 604/93.01 |
| 6,389,310 B1 * | 5/2002 | Demonceau et al. | 600/512 |
| 6,454,712 B1 * | 9/2002 | Oonuki | 600/437 |
| 8,046,707 B2 * | 10/2011 | Akaki | 715/767 |
| 2004/0207661 A1 * | 10/2004 | Akaki | 345/764 |
| 2006/0211909 A1 * | 9/2006 | Anstadt et al. | 600/16 |
| 2007/0014452 A1 * | 1/2007 | Suresh et al. | 382/128 |
| 2007/0031019 A1 * | 2/2007 | Lesage et al. | 382/131 |
| 2007/0167771 A1 | 7/2007 | Olstad | |
| 2009/0281424 A1 | 11/2009 | Friedman et al. | |
| 2011/0021915 A1 * | 1/2011 | Feng et al. | 600/443 |

FOREIGN PATENT DOCUMENTS

| | | |
|---|---|---|
| EP | 2026280 A1 | 2/2009 |
| JP | 10165401 A | 6/1998 |
| WO | 9955233 A | 11/1999 |

OTHER PUBLICATIONS

D.C. Wilson, E.A. Geiser, D.A. Conetta, J.M. Murphy, Dongxing Wang; Abstract : "An Automated Algorithm for Analysis of 2-D Echocardiographic Short-Axis Images: A Brief Overview," mmbia, pp. 0222, 1996 Workshop on Mathematical Methods in Biomedical Image Analysis (MMBIA '96), 1996; 2 Pages.

Christian H. P. Jansen, Muthuvel Arigovindan, Michael Sühling, Stefan Marsch, Michael Unser and Patrick Hunziker; Multidimensional, multistage wavelet footprints: a new tool for image segmentation and feature extraction in medical ultrasound; URL : http://bigwww.epfl.ch/publications/jansen0301.html; 6 Pages.

(Continued)

*Primary Examiner* — Baisakhi Roy
(74) *Attorney, Agent, or Firm* — Scott J. Asmus

(57) ABSTRACT

A method for automatically measuring interventricular septum thickness is provided. The method in one embodiment comprises acquiring a series of ultrasound images of a heart, acquiring a septum mask by applying a septum segmentation algorithm on the series of ultrasound images, localizing a mitral valve tip using a valve tip localization algorithm and calculating the thickness of the interventricular septum using an interventricular septum thickness algorithm. The interventricular septum thickness algorithm uses the septum mask and the localized mitral valve tip as inputs.

13 Claims, 18 Drawing Sheets

(56) References Cited

OTHER PUBLICATIONS

Hassan Moladoust, Manijhe Mokhtari-Dizaji, Zahra Ojaghi-Haghighi, Fereydon Noohi, Arsalan Khaledifar and Hadi Grailu; Determination of Instantaneous Intraventricular Septum Wall Thickness by Procesing Sequential 2D Echocardiographic Images; Pakistan Journal of Biological Sciences 10 (3): pp. 454-461, 2007.

Martin, S. Daanen, V. Troccaz, J. Chavanon, O; Abstract : Tracking of the mitral valve leaflet in echocardiography images; Biomedical Imaging: Nano to Macro, 2006. 3rd IEEE International Symposium; Issue Date: Apr. 6-9, 2006; on pp. 181-184; Location: Arlington, VA; Print ISBN: 0-7803-9576-X; INSPEC Accession No. 9073092; Date of Current Version: May 8, 2006.

* cited by examiner

METHODS AND APPARATUS FOR AUTOMATED MEASURING OF THE INTERVENTRICULAR SEPTUM THICKNESS

BACKGROUND

The subject matter disclosed herein relates generally to ultrasonic diagnostic systems and, in particular to a method and apparatus for automated measuring of the interventricular septum thickness.

Measuring the thickness of interventricular septum in diastole (IVSd) is accepted as one of the cornerstone measurements in echocardiography since it is, along with left ventricle size, one of the main indicators of cardiac hypertrophy. As cardiac hypertrophy potentially leads to other cardiac complications, the measurement of the thickness of IVSd can be used for screening purposes. Further, the thickness of IVSd has also shown a correlation to 24 h ambulatory blood pressure.

The manual measurement protocol specifies that measurement of thickness of IVSd should be carried out along a measurement line that is orthogonal to the center line of the septum region and passing through the mitral valve tip. However, conventional manual measurement of the septum thickness suffers from observer variability based on the experience of the observer. For example, the septum thickness measurement varies with different observers. Furthermore, the septum thickness measurement usually varies for the same observer at different instances. Such variability in the measurement of septum thickness can lead to variations, which may cause erroneous diagnoses. For example, erroneous diagnosis may lead to hypertrophic subjects being classified as healthy, and healthy subjects being classified as hypertrophic, both of which have undesirable consequences.

Therefore, there is a need in the art for an apparatus and method for managing or controlling the variability in measuring the thickness of IVSd.

BRIEF DESCRIPTION

A method for automated measuring of thickness of interventricular septum in diastole is provided. The method in one embodiment comprises acquiring a series of ultrasound images of a heart, acquiring a septum mask by applying a septum segmentation algorithm on the series of ultrasound images, localizing a mitral valve tip using a valve tip localization algorithm and calculating the thickness of the interventricular septum using an interventricular septum thickness algorithm. The interventricular septum thickness algorithm uses the septum mask and the localized mitral valve tip as inputs.

An apparatus for automated measuring of interventricular septum thickness is provided. The apparatus according to one embodiment comprises a transducer that acquires a series of ultrasound images of a heart, and a central processor. The central processor is configured to acquire a septum mask by applying a septum segmentation algorithm on the series of ultrasound images, localizing a mitral valve tip using a valve tip localization algorithm, and calculating the thickness of the interventricular septum using a interventricular septum thickness algorithm. The interventricular septum thickness algorithm uses the septum mask and the localized mitral valve tip as inputs.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
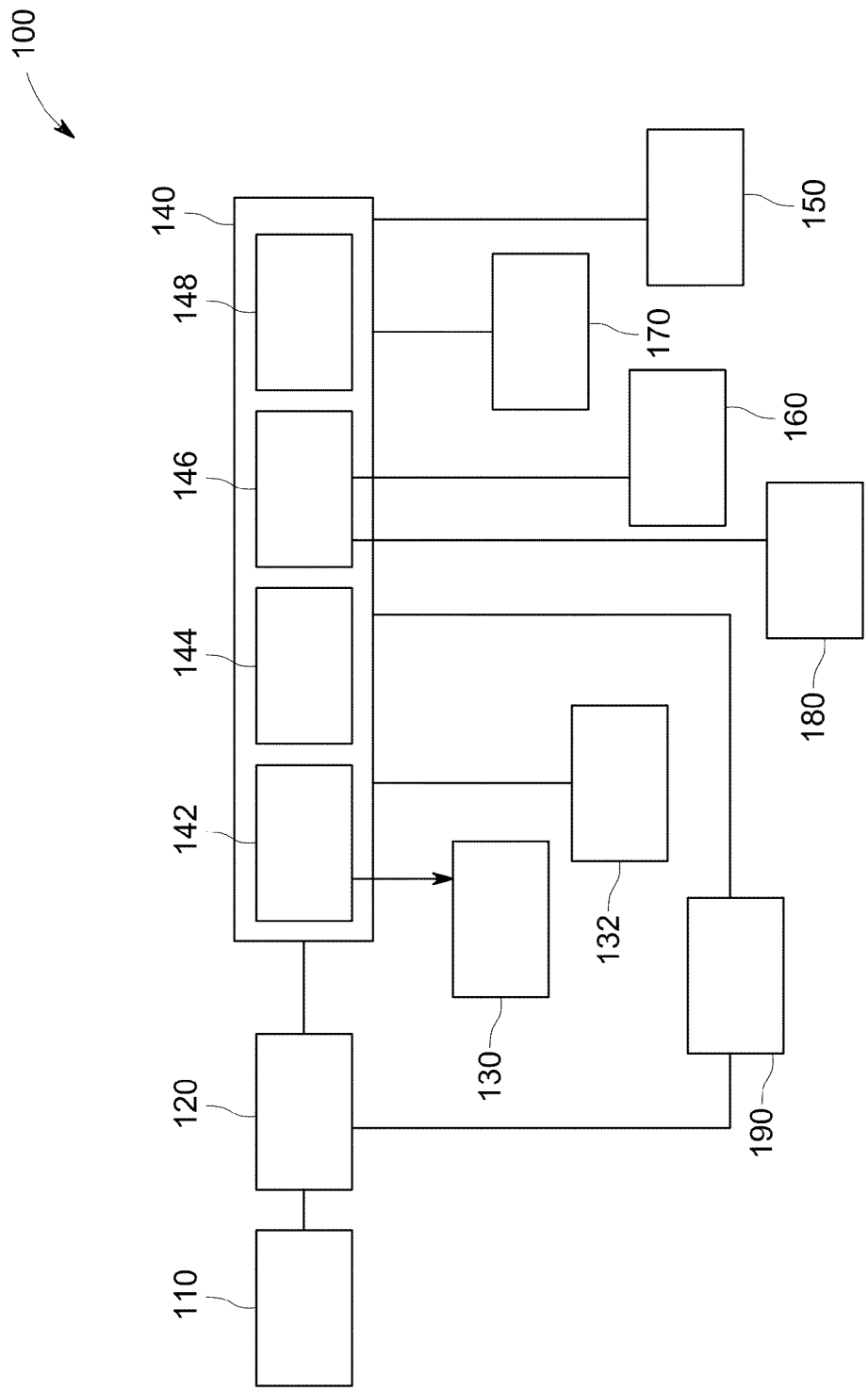
FIG. 1 is a schematic representation of an ultrasound apparatus for automated measurement of interventricular septum thickness, according to an embodiment of the present system.

FIG. 1 is a schematic representation of an ultrasound apparatus 100 for automated measurement of thickness of interventricular septum in diastole (IVSd), according to an embodiment of the present system. The ultrasound apparatus 100 comprises a transducer array 110, a transmit/receive (T/R) processor such as a T/R ASIC 120, a processing section such as a processing ASIC 140 and a power source 190. Peripheral components are typically coupled to the processing ASIC 140. The T/R ASIC 120 drives the elements of the transducer array 110 and receives echoes received by the elements. The T/R ASIC 120 also controls the transmit and receive apertures of the transducer array 110 and the gain of the received echo signals. Echoes received by the T/R ASIC 120 are provided to the processing ASIC 140, which beamforms the echoes from the individual transducer elements into scanline signals. The processing ASIC 140 also controls the transmit waveform, timing, aperture and focusing. Further, the processing ASIC provides timing signals for time gain control and, monitors and controls the power supplied to the transducer array 110. A memory device 150 is connected to the processing ASIC 140, which stores data used by the beamforming processing ASIC 140. Those skilled in the art will appreciate that the various ASICs comprising the ultrasound apparatus 100 is only by way of example and not limiting. The functions of the ASICs comprising the ultrasound system 100 could be provided by a field-programmable gate array (FPGA), an ARM processor or a higher order processor such as a multi-CPU that performs multiple functions among others.

In the illustrated embodiment, the processing ASIC 140 further comprises a scan conversion module 142, a Digital Signal Processing Unit (DSPU) 144, a controller 146 and a central processor 148. Beamformed scanline signals are coupled to the DSPU 144, wherein the DSPU 144 filters the scanline signals and ultrasound B mode information is coupled to a scan conversion module 142 for scan conversion and the production of video output signals. The processing ASIC 140 in one example also adds alphanumeric information to the display such as the time, date and patient identification. A graphics processor (not shown) overlays the ultrasound image with information such as depth and focus markers and cursors. Frames of ultrasonic images are typically stored in a video memory 130 coupled to the processing ASIC 140, enabling them to be recalled and replayed such as in a live Cineloop® realtime video sequence. This video information can be communicated as a video output in several formats, for example, NTSC and PAL television formats, RGB drive signals for an LCD display 132, among other video display formats. The central processor 148 is configured to execute ultrasound data analysis routines, for example, a method 200 for measuring thickness of IVSd discussed with reference to FIG. 2.

The controller 146 is coupled to the central processor 148 and the DSPU 144, and the controller 146 controls and synchronizes the processing and control functions throughout the ultrasound apparatus 100. The controller 146 is also coupled to a user control 180 to accept user inputs, and directs and controls operations of the ultrasound apparatus 100. A program memory 160 is coupled to the processing ASIC 140 and stores software routines that are usable by the controller 146, for example, to operate and control the ultrasound apparatus 100.

The processing ASIC 140 is also coupled to a data port, which in this example is configured as a PCMCIA interface 170. The interface 170 allows other modules and functions to be attached to the ultrasound apparatus 100. The interface 170 for example, can connect to a modem or other communication links to transmit and receive ultrasound information to/from remote locations.

Power for the ultrasound apparatus is provided by a power source 190. The power source may include a converter to convert the voltage supplied by the power source to a suitable voltage required by T/R ASIC 120 to drive the elements of the transducer array 110.

The architecture of the ultrasound apparatus 100 may be designed such that the ultrasound apparatus may be large and mountable on a cart for portability, the size of a desktop or the size of a hand-held device such as a mobile phone.

In one embodiment, the ultrasound apparatus 100 is a hand-held device. Automated method of measurement of thickness of IVSd is advantageously exploited, when the ultrasound apparatus 100 is a hand-held device, as the hand-held device provides extreme flexibility and wide application of the automated method of measurement of thickness of IVSd. The ultrasound apparatus 100 is packaged as a hand-held device through judicious selection of functions and features and the efficient use of integrated circuits and ultrasound technology. As an example and not as a limitation, of judicious use of integrated circuits, the controller 146 is a RISC (reduced instruction set controller) processor in the ultrasound apparatus 100 packaged as a hand-held device.

Figure 2:
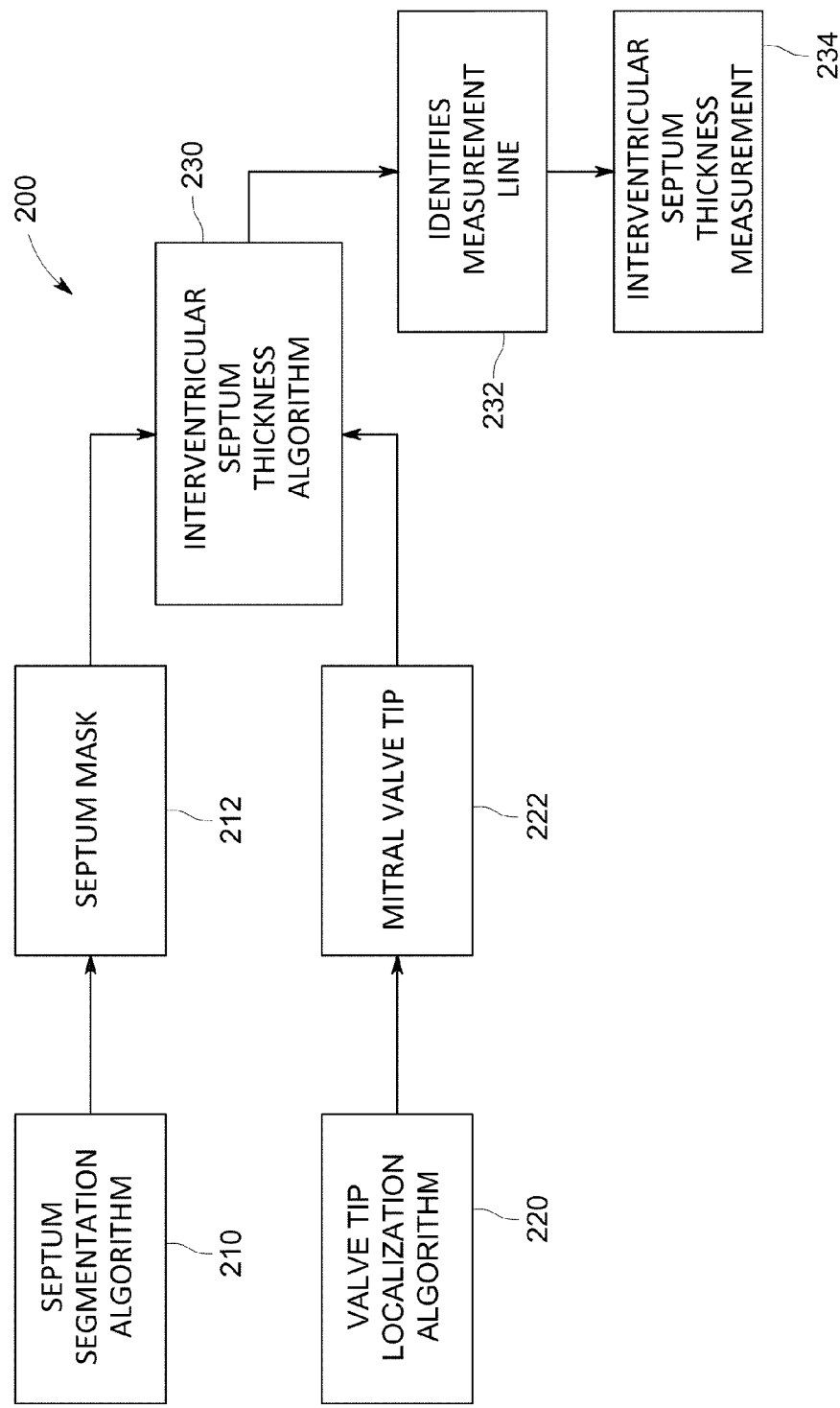
FIG. 2 is a flow diagram illustrating a method for automated measuring of interventricular septum thickness, according to an embodiment of the present method.

FIG. 2 is a flow diagram illustrating a method 200 for automated measuring of thickness of IVSd, according to one embodiment of the present disclosure. The method 200 begins with an Interventricular Septum Segmentation Algorithm (ISSA) at step 210 and a Valve Tip Localization Algorithm (VTLA) at step 220. At step 210, images of interventricular septum acquired using an ultrasound apparatus, similar to for example ultrasound apparatus 100 of FIG. 1, are segmented using the ISSA. At step 212, the ISSA provides a septum mask. The Interventricular Septum Segmentation Algorithm (ISSA) is described in further detail with reference to FIG. 3, and illustrative images are provided for certain steps in FIG. 4a, FIG. 4b and FIG. 4c. At step 220, the mitral valve tip is localized by applying the Valve Tip Localization Algorithm (VTLA) on a sequence ultrasound images acquired using an ultrasound apparatus, similar to for example ultrasound apparatus 100 of FIG. 1. At step 222, the VTLA provides the mitral valve tip location. The Valve Tip Localization Algorithm (VTLA) is described in detail later in method 222 with reference to FIG. 5a, FIG. 5b and illustrative images for certain steps in FIG. 6a, FIG. 6b and FIG. 6c.

At step 230, both, the interventricular septum mask and localized mitral valve tip are provided as inputs to the interventricular septum thickness algorithm or IVST algorithm. Those skilled in the art will appreciate that the order of measurements for obtaining interventricular septum mask and localized mitral valve tip described herein are not restrictive and only illustrative. For example, first the interventricular septum mask may be acquired followed by the localized mitral valve tip. Subsequently, at step 230, both, the interventricular septum mask and localized mitral valve tip are provided as inputs to the IVST algorithm. At step 232, the IVST algorithm identifies a measurement line. The measurement line is identified such that the measurement line is orthogonal to a central line of the interventricular septum and passes through the tip of the mitral valve. At step 234, the IVST algorithm calculates the thickness of IVSd. Thickness of IVSd is calculated as the distance between the points of intersection between the measurement line and the septum mask. The IVST algorithm is described in further detail with reference to FIG. 7 and illustrative images steps in FIG. 8a, FIG. 8b, FIG. 8c and FIG. 8d.

Figure 3:
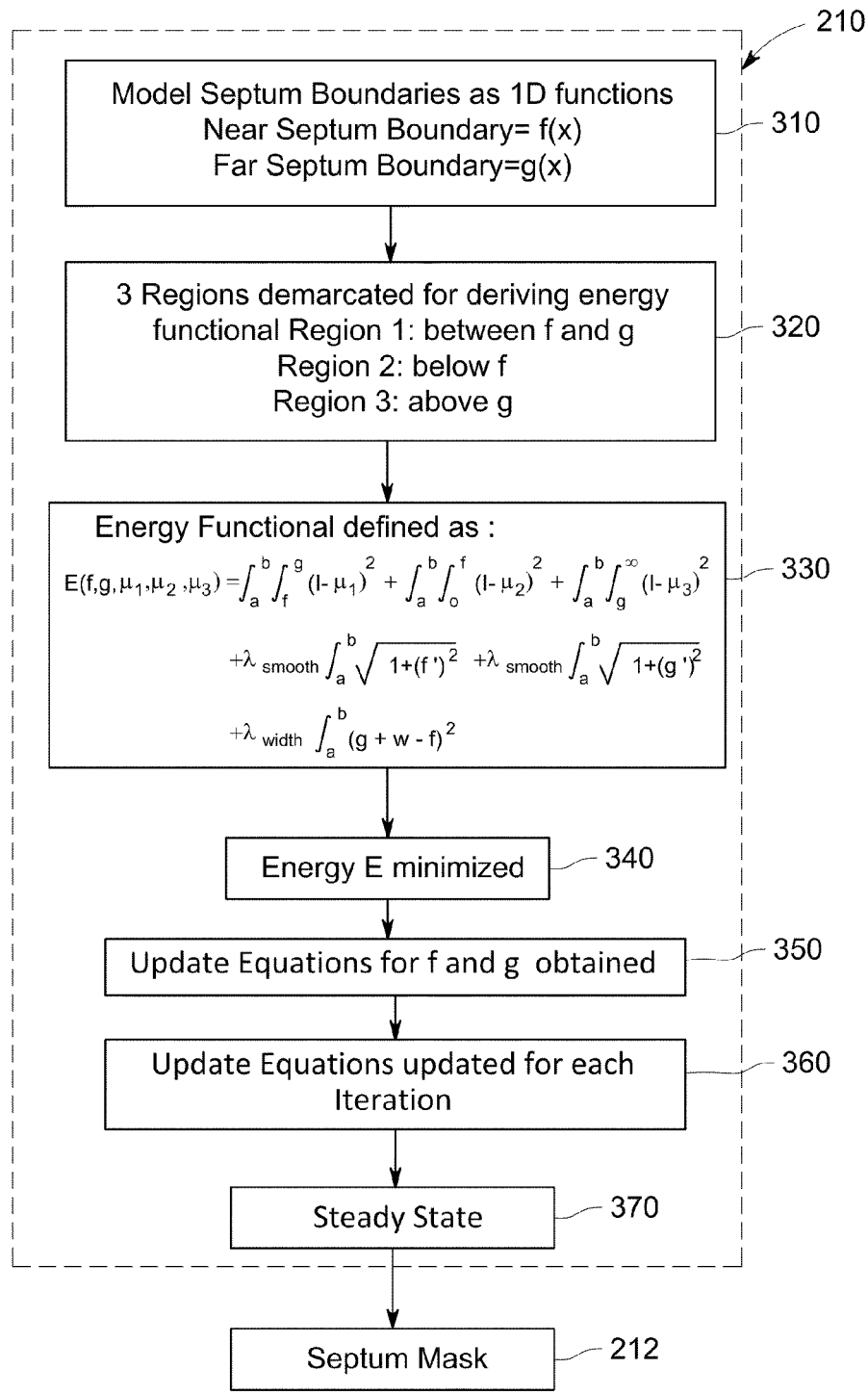
FIG. 3 is a flow diagram illustrating a method of interventricular septum segmentation, according to an embodiment of the present method.

FIG. 3 is a flow diagram illustrating a method 210 of interventricular septum segmentation according to an embodiment of the present disclosure. The method 210 describes the Interventricular Septum Segmentation Algorithm (ISSA) in further detail. The method 210 begins at step 310, at which the interventricular septum boundaries are represented as two separate one dimensional profiles. The interventricular septum boundary that is proximal to the mitral valve is referred to as the near septum boundary, and is represented as a one dimensional profile f(x). The interventricular septum boundary that is distal to the mitral valve is referred to as the far septum boundary, and is represented as a one dimensional profile g(x).

Figure 4A:
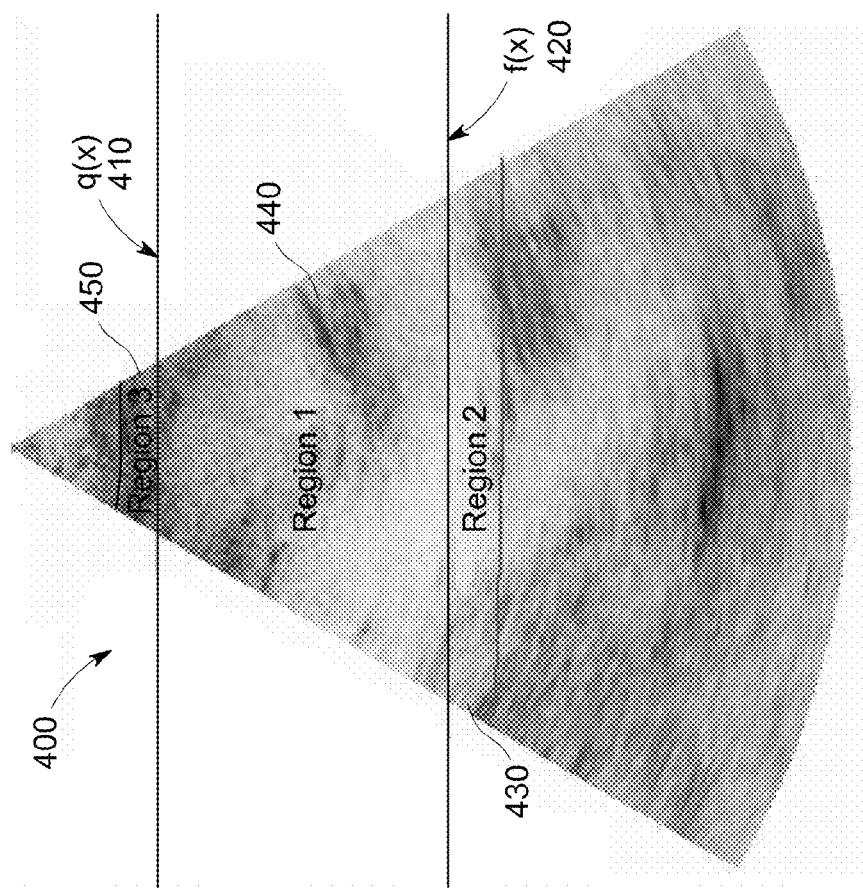
FIG. 4a is a Parasternal Long Axis (PLAX) view ultrasound image of the interventricular septum illustrating initialization of two one-dimensional functions to represent interventricular septum boundaries and three regions demarcated by interventricular septum segmentation algorithm, according to one embodiment.
Figure 4B:
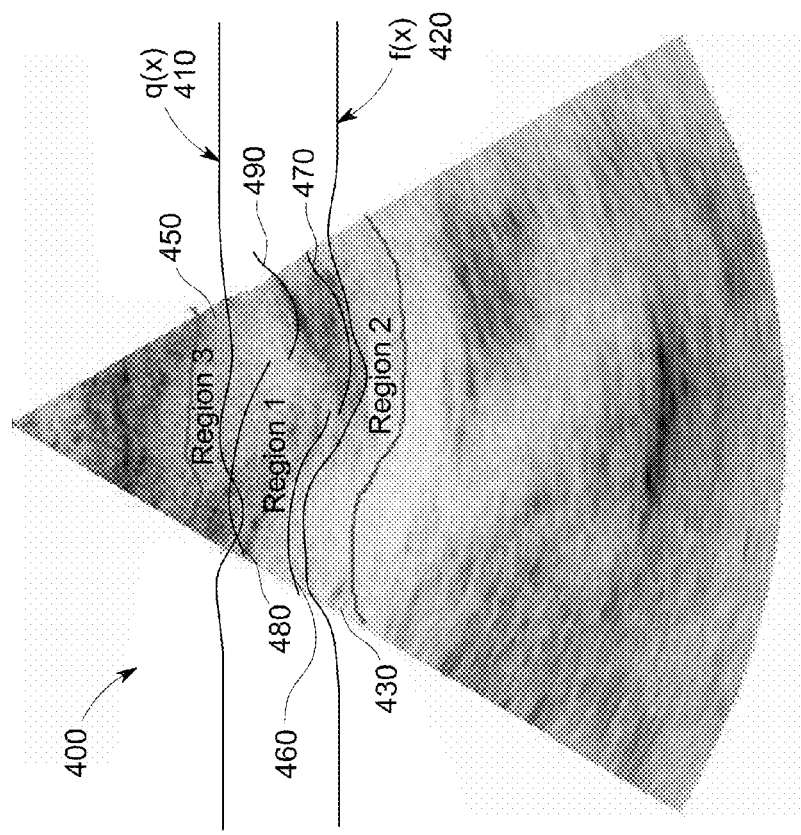
FIG. 4b is a PLAX view ultrasound image of the interventricular septum illustrating an intermediate iteration of the interventricular septum segmentation algorithm, according to a further embodiment.
Figure 4C:
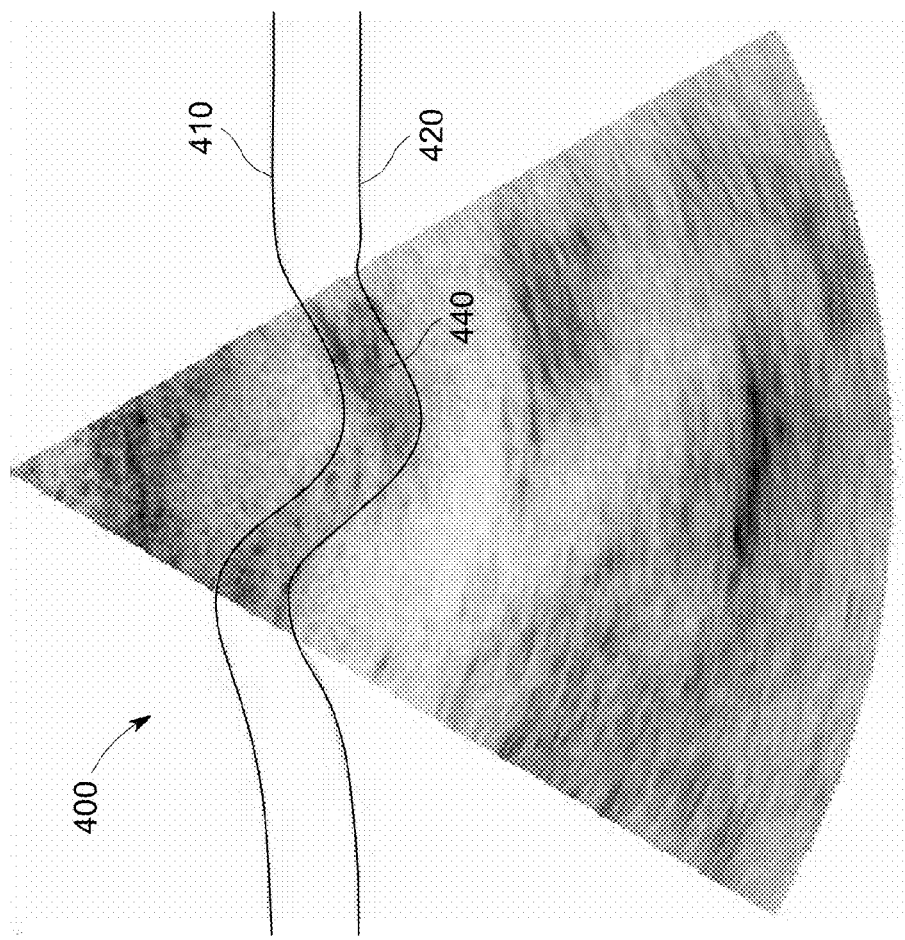
FIG. 4c is a PLAX view ultrasound image of the interventricular septum illustrating convergence of energy function, according to a further embodiment.

Subsequently, at step 320 the ISSA demarcates the ultrasound image of the septum into multiple regions, which in one example is divided into three regions. The three regions include a Region 1, a Region 2 and a Region 3. The three regions are illustrated in FIG. 4a-4c, described in further detail below. Further, at step 330, the ISSA defines an energy function for the septum mask that is a combination of local region intensity statistics and shape constraints. The shape constraints further comprise smoothness and width constraints The energy function is given by:

$$E(f, g, \mu_1, \mu_2, \mu_3) =$$
$$\int_a^b \int_f^g (I-\mu_1)^2 + \int_a^b \int_0^f (I-\mu_2)^2 + \int_a^b \int_g^\infty (I-\mu_3)^2 +$$
$$\lambda_{smooth} \int_a^b \sqrt{1+(f')^2} + \lambda_{smooth} \int_a^b \sqrt{1+(g')^2} + \lambda_{width} \int_a^b (g+w-f)^2$$

The variables $\mu_1$, $\mu_2$ and $\mu_3$ are the respective mean intensities of the Region 1, Region 2 and Region 3 respectively. The variable w is a constant for the septum thickness, that is estimated, and in one example is 1 centimeter. The evolution of the septum mask is guided by the solution that minimizes the energy. At step 340, $\nabla E$ is set to 0. As a result, at step 350 the following update equations for the functions f and g are obtained:

$$f^{(n+1)} =$$
$$f^{(n)} - dt \sum_{m=1}^{M} \left[ (I-\mu_2(m))^2 - (I-\mu_1(m))^2 - \lambda_{smooth} \left( \frac{f'}{\sqrt{1+(f')^2}} \right)' - \lambda_{width}(g+w-f) \right]$$

$$g^{(n+1)} = g^{(n)} - dt \sum_{m=1}^{M} \left[ (I-\mu_1(m))^2 - (I-\mu_3(m))^2 - \lambda_{smooth} \left( \frac{g'}{\sqrt{1+(g')^2}} \right)' - \lambda_{width}(g+w-f) \right]$$

The variable M denotes the number of segments of f(x) and/or g(x). The solution in one example is obtained iteratively, and is generally solved through variational calculus methods. At step 360, the equations are updated for each iteration. Specifically, in one embodiment a gradient descent is performed until convergence of the septum mask, while updating the near septum boundary profile and the far septum boundary profile in each iteration. At step 370, a steady state is achieved, with convergence or termination criterion either, a predetermined number of iterations, or achievement of a steady state, for example. A steady state is generally considered to be achieved when mean function displacements for consecutive iterations are below a predetermined threshold. As noted in FIG. 2, at step 212, the septum mask is obtained.

FIG. 4a is a Parasternal Long Axis (PLAX) view ultrasound image 400 of the interventricular septum illustrating initialization of two one-dimensional functions to represent interventricular septum boundaries and three regions demarcated by interventricular septum segmentation algorithm, according to one embodiment. The initialization of the two one dimensional profiles representing the interventricular septum boundaries, for example at step 310 of FIG. 3 is illustrated in FIG. 4a. In the illustrated embodiment, the near septum boundary is represented as f(x) 410. Similarly, the far septum boundary is represented as g(x) 420.

Further, the three regions demarcated by the ISSA for example at step 320 of FIG. 3, in the illustrated embodiment include, a Region 1 440, Region 2 430 and Region 3 450. The line markings depicting for example, the boundaries of the Region 2 230 and the Region 3 450, are for illustration only and not the actual regions used in computation by the ISSA. The Region 1 440 represents the septum region that is between the near septum boundary 420 and the far septum boundary 410. The Region 2 430 represents the area below the near septum boundary 420. The Region 3 represents the area above the far septum boundary 410.

FIG. 4b is a PLAX view ultrasound image 400 of the interventricular septum illustrating an intermediate iteration of the ISSA, for example at step 350 of FIG. 3, according to an embodiment of the present disclosure. In the illustrated embodiment, a prior iteration segment 460 illustrates a segment of the near septum boundary 420 at iteration n−1. A later iteration segment 470 illustrates a segment of the near septum boundary 420 at iteration n. Similarly, a prior iteration segment 480 illustrates a segment of the far septum boundary 410 at iteration (n−1). A later iteration segment 490 illustrates a segment of the far septum boundary 410 at iteration n.

FIG. 4c is a PLAX view ultrasound image 400 of the interventricular septum illustrating convergence of energy function, for example at step 370 of FIG. 3, according to an embodiment of the present disclosure. On convergence of the energy function, ISSA provides the septum mask. In the illustrated embodiment, the septum mask is clearly defined with the near septum boundary 420 and the near septum boundary 410.

Figure 5A:
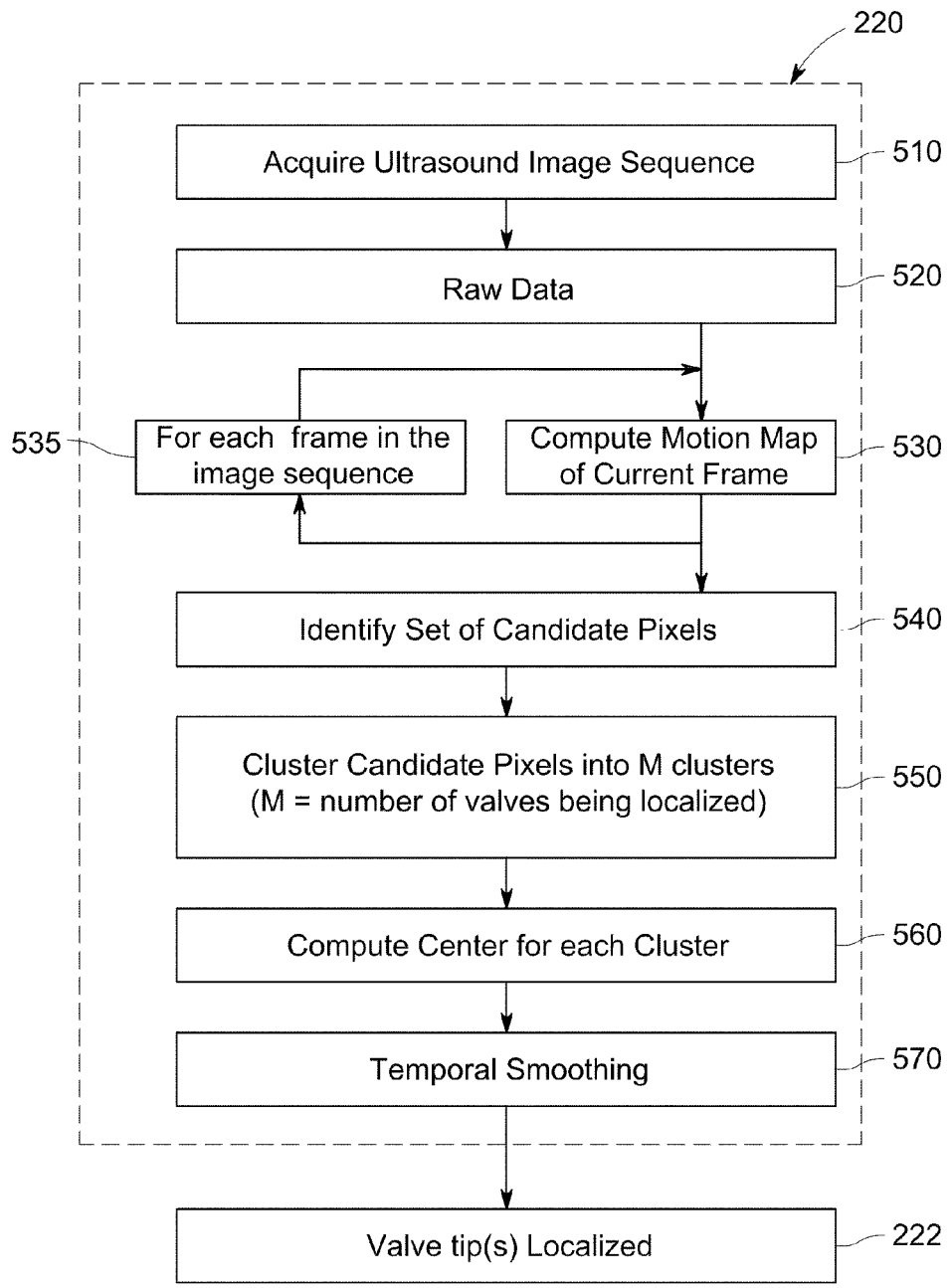
FIG. 5a is a flow diagram illustrating a method for valve tip localization, according to an embodiment of the present technique.

FIG. 5a is a flow diagram illustrating a method for valve tip localization, according to an embodiment of the present disclosure. The method 220 describes the VTLA processing in detail. The method 220 begins at step 510 at which a sequence of ultrasound images of an internal anatomical structure, for example, a heart is acquired. Those skilled in the art will appreciate that images acquired at step 510 are ultrasound images of the internal anatomical structure that allow visualization of the valves of the internal anatomical structure. For example, the images acquired at step 510 are PLAX views or 4CH views, among other views of ultrasound images of the heart. At step 520, the raw data from the sequence of images is passed on to the VTLA for processing by for example, the central processor 148 of FIG. 1. At step 530, the VTLA computes a motion map for a current frame. Computing the motion map involves computing successive frame differences. The frame difference is computed based on either the difference between the current frame and previous frame or the difference between the current frame and the next frame. Computing the motion map in one example is based on frame differences and provides economy in computation time that is suitable for automated measuring of the thickness of IVSd.

Further, at step 535, the VTLA computes a motion map for each frame in the sequence of acquired ultrasound images. According to an embodiment of the present disclosure, the VTLA computes successive frame differences. The successive frame differences are for example computed according to the following representative logic:

```
Given-
1) frameNumber : The current frame of which the septum measurement
   needs to be performed.
2) frameOffset : Difference between number of current and next/previous
   frames
prevFrameNumber ← frameNumber – frameOffset
nextFrameNumber ← frameNumber + frameOffset
if prevFrameNumber refers to a valid frame
    compare current frame and previous frame
if nextFrameNumber refers to a valid frame
    compare current frame and next frame
```

At step 540, the VTLA identifies a set of candidate pixels for each frame. The number of candidate pixels identified in the set of candidate pixels is a predetermined number such as, for example 100 candidate pixels. Candidate pixels are identified by considering those pixels in the frame that have high magnitude of frame differences in order to capture locations corresponding to high motion. For example, the candidate pixels are identified considering the curr_prev_FrameDiff and next_curr_FrameDiff. Further, the VTLA prunes and refines the set of candidate pixels using constraints such as region of interest (ROI).

At step 550, the VTLA clusters the set of candidate pixels into M clusters, where M is the number of valve tips being localized by VTLA. Any known means of clustering such as for example, k-means clustering may be used to cluster the set of candidate pixels. Subsequently, at step 560, the VTLA computes a cluster centre. The cluster centre is computed by using techniques generally known in the art, such as, for example, the cluster centre may be computed based on the median of the set of candidate pixels. The cluster centre represents the mitral valve tip location. At step 570, the VTLA computes a smoothed location of the mitral valve tip by using temporal smoothing. The representative location of the mitral valve tip is refined by computing an average of the representative location of the mitral valve tip from previous frames.

Figure 5B:
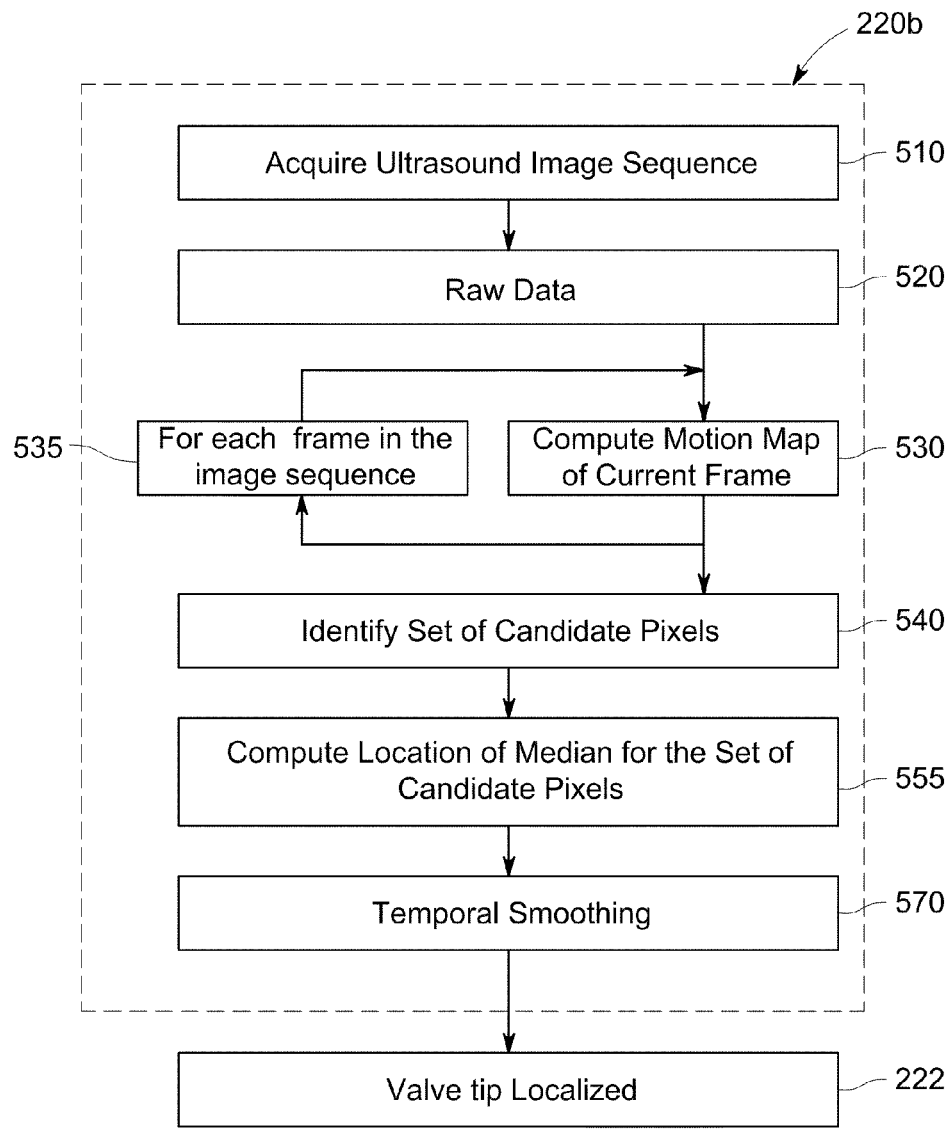
FIG. 5b is a flow diagram illustrating a method for one valve tip localization, according to an embodiment of the present technique.

FIG. 5b is a flow diagram illustrating a method for one valve tip localization, according to an embodiment of the present technique. Similar to the method 200, the method 220b begins at step 510 at which a sequence of ultrasound images are acquired. The sequence of images acquired at step 510 is for example, parasternal long axis (PLAX) view images in B mode. PLAX view images are acquired as the B mode has a high frame rate capability for the widest field of view and high image resolution. Additionally, PLAX view provides a good visualization of the mitral valve.

At step 520, the raw data from the sequence of images is passed on to the VTLA for processing and at step 530, the VTLA computes a motion map for a current frame. Further, at step 535, the VTLA computes a motion map for each frame in the sequence of acquired ultrasound images. At step 540, the VTLA identifies a set of candidate pixels for each frame.

At step 555, the method 220b differs from the method 220. Since method 220b is simplified for localization of one valve, the clustering at step 550 of method 200 is approximated with a simple median computation at step 555. At step 555, a median location of the candidate pixels is computed. Subsequently, at step 570, the VTLA computes a smoothed location of the mitral valve tip by using temporal smoothing. The method 220b, simplified for localization of one valve in PLAX view ultrasound image of the heart allows for a fast real-time implementation of the VTLA.

Figure 6A:
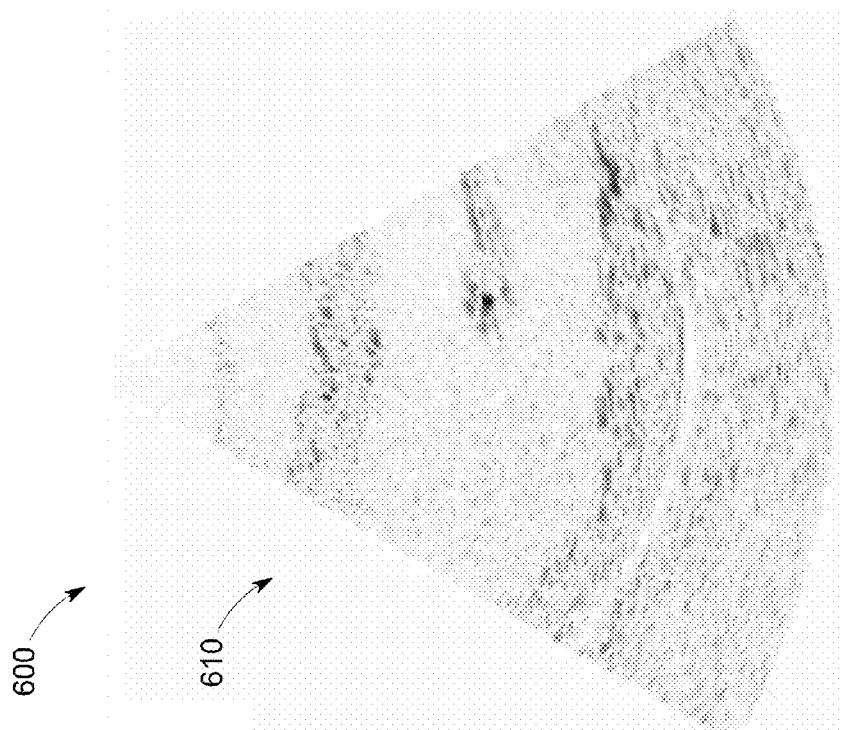
FIG. 6a illustrates a frame difference between a current PLAX view ultrasound image of the heart and a previous PLAX view ultrasound image of the heart, according to one embodiment.

FIG. 6a illustrates a frame difference 600 between a current PLAX view ultrasound image of the heart and a previous PLAX view ultrasound image of the heart, according to one embodiment. Although, in the illustrated embodiment, the frame difference 600 is a difference between the current PLAX view ultrasound image and the previous PLAX view ultrasound image of the heart, frame difference between the current PLAX view ultrasound image and a subsequent PLAX view ultrasound image is also used to obtain frame differences. Such frame differences are used by the VTLA to compute a motion map for a current frame, for example at step 530 of FIG. 5a and FIG. 5b.

Figure 6B:
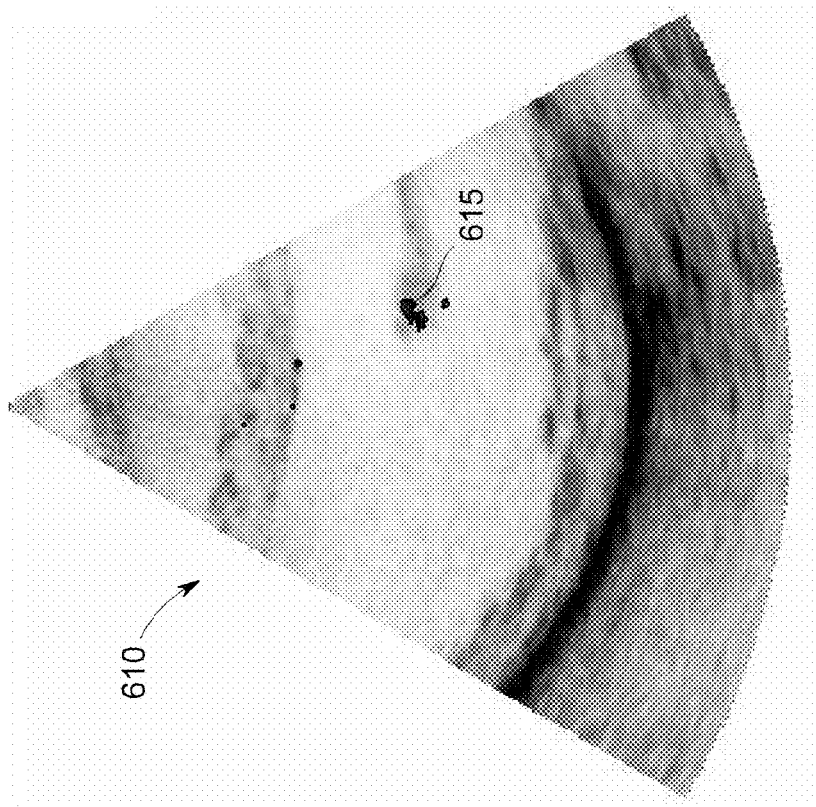
FIG. 6b is a PLAX view ultrasound image of the heart illustrating a set of candidate pixels, according to a further embodiment.

FIG. 6b is a PLAX view ultrasound image of the heart illustrating a set of candidate pixels, according to a further embodiment. In the illustrated embodiment, the PLAX view ultrasound image of the heart represents a current frame 610, and a set of candidate pixels 615 identified and pruned by the VTLA, for example at step 540 of method 220b illustrated in FIG. 5b.

Figure 6C:
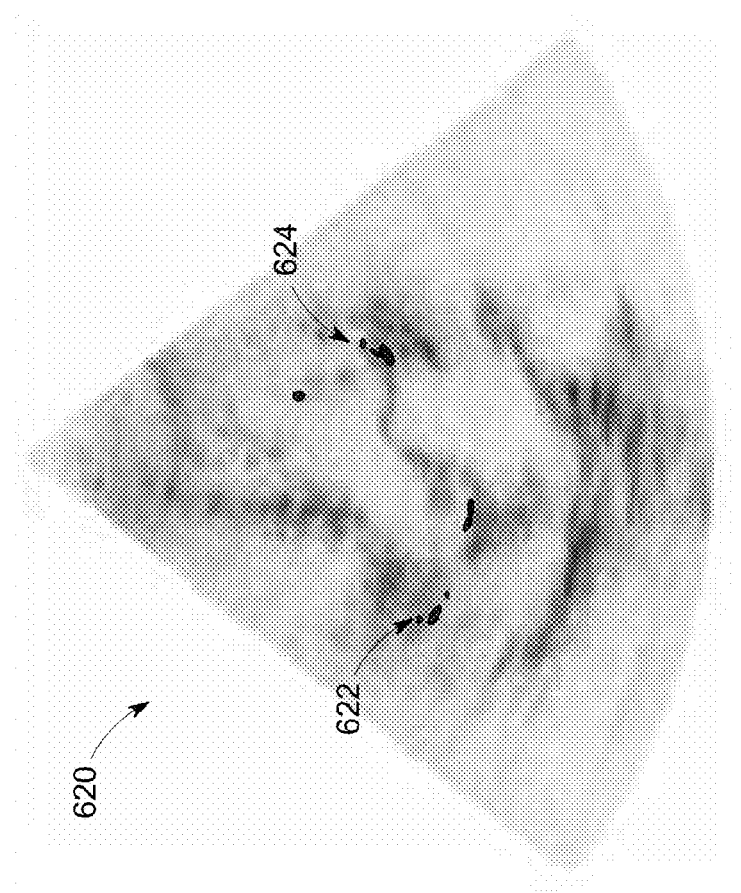
FIG. 6c is a 4CH view ultrasound image of the heart illustrating two clusters for the two valve tips, according to one embodiment.

FIG. 6c is a 4CH view ultrasound image of the heart illustrating two clusters for the two valve tips, according to one embodiment. In the illustrated embodiment, the 4CH view ultrasound image of the heart represents a current frame 620, with the set of candidate pixels clustered into 2 clusters 622 and 624 for two valve tips localized by the VTLA, for example at step 550 of the method 220 illustrated in FIG. 5a.

Figure 6D:
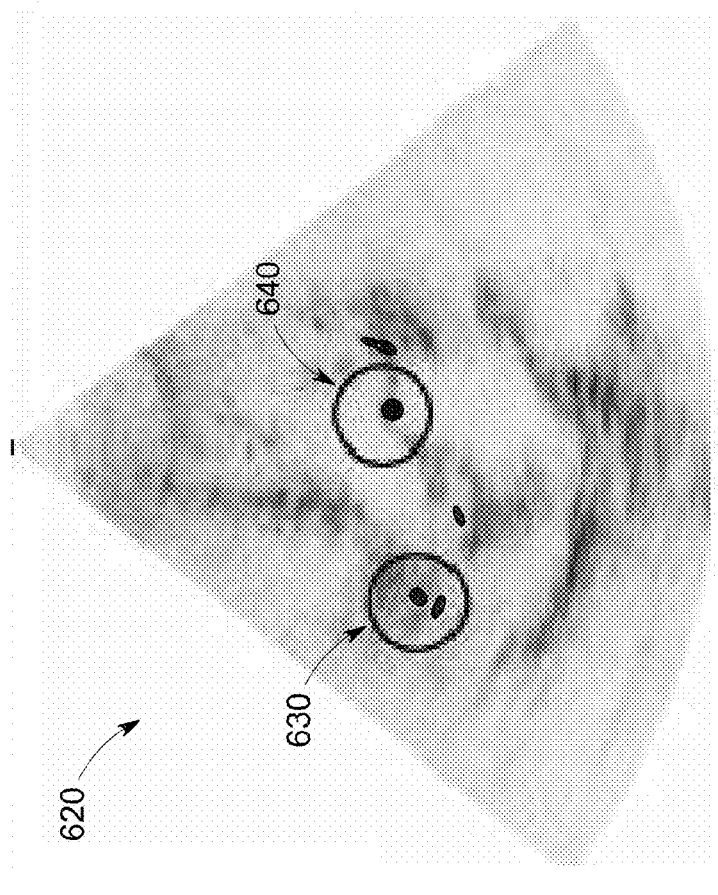
FIG. 6d is a 4CH view ultrasound image of the heart illustrating two valve tips localized, according to one embodiment.

FIG. 6d is a 4CH view ultrasound image of the heart illustrating two valve tips localized, according to one embodiment. In the illustrated embodiment, the 4CH view ultrasound image of the heart represents the current frame 620, and two valve tips 630 and 640 localized by the VTLA, for example at step 222 of the method 220 illustrated in FIG. 5a. The two valve tips 630 and 640 are localized by computing the cluster centers for the clusters 622 and 624 respectively, for example at step 560 of the method 220 illustrated in FIG. 5a.

Figure 6E:
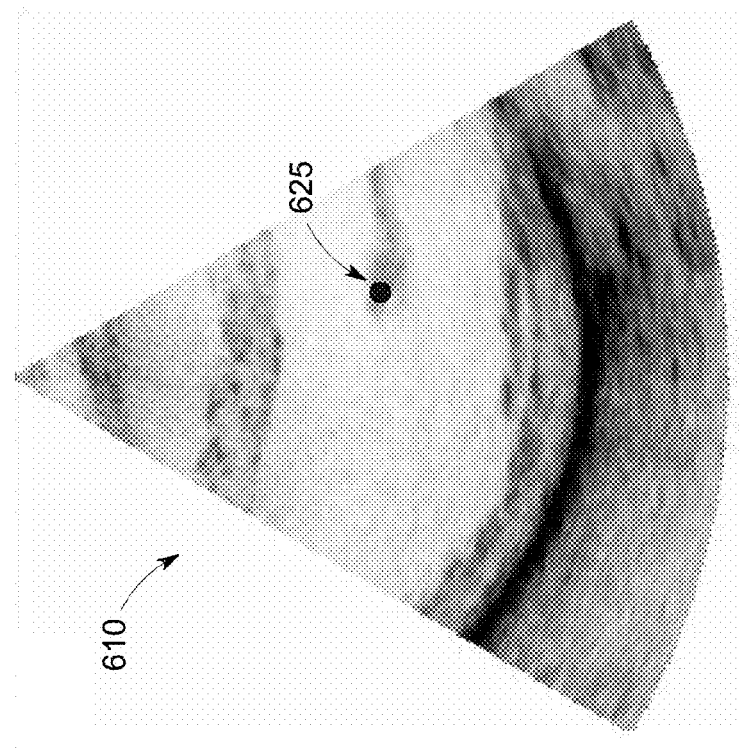
FIG. 6e is a PLAX view ultrasound image of the heart illustrating the mitral valve tip localized, according to a further embodiment.

FIG. 6e is a PLAX view ultrasound image of the heart illustrating the mitral valve tip localized, according to one embodiment. In the illustrated embodiment, the PLAX view ultrasound image of the heart represents the current frame 610, and the mitral valve tip 625 localized by the VTLA, for example at step 222 of the method 220b of FIG. 5b. The mitral valve tip 625 is localized by computing the location of the median for the candidate pixels, for example, similar to candidate pixels 615 of FIG. 6b, for example, at step 555 of the method 220b illustrated in FIG. 5b.

Figure 7:
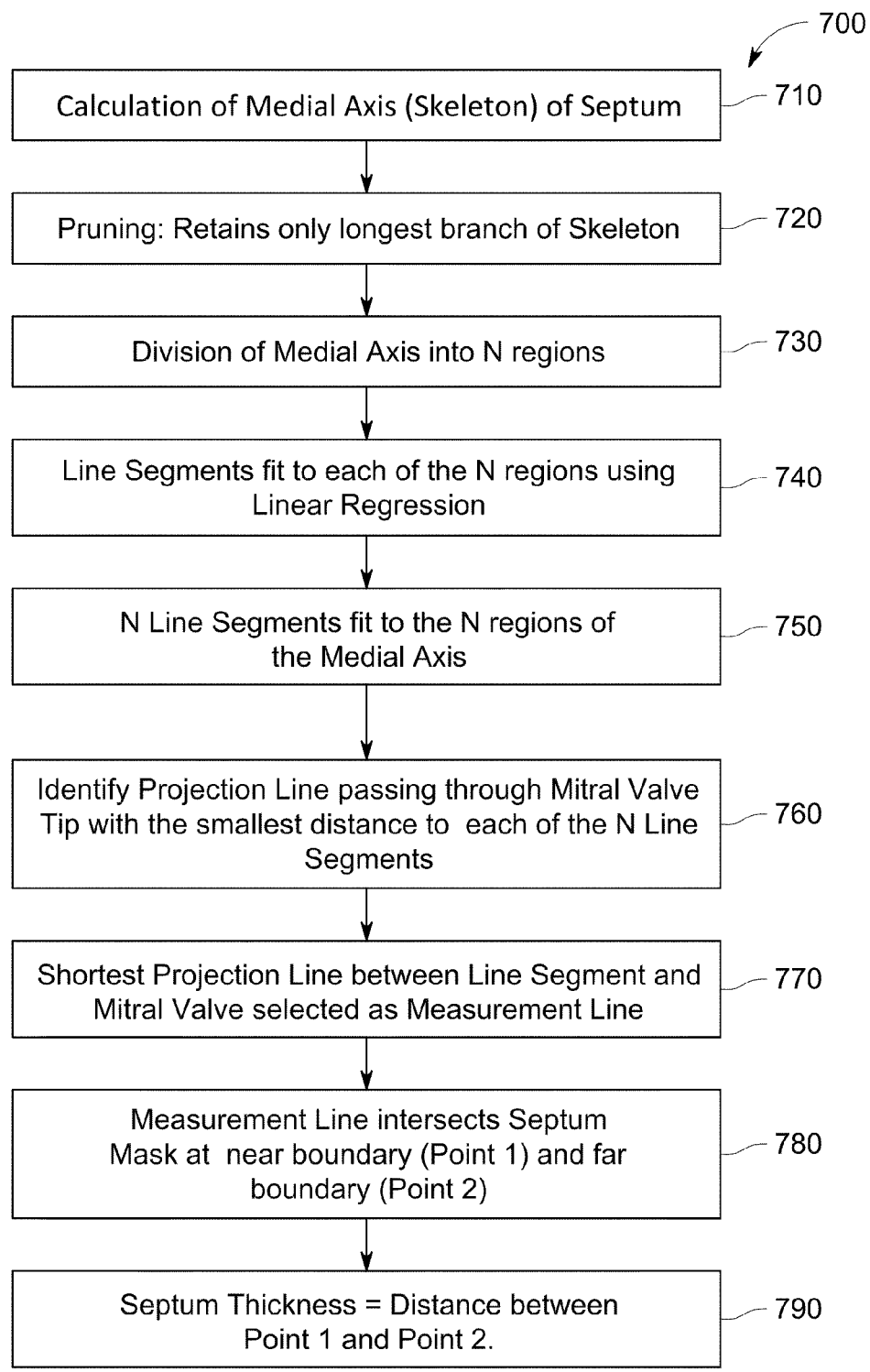
FIG. 7 is a flow diagram illustrating a method for measuring interventricular septum thickness, according to one embodiment.

FIG. 7 is a flow diagram illustrating a method 700 for measuring interventricular septum thickness, according to one embodiment. The method 700 describes the IVST algorithm processing in detail. The method 700 begins at step 710 at which the IVST algorithm, calculates an interventricular septum skeleton or the medial axis of the interventricular septum. Any of the standard skeletonization algorithms may be employed for calculating the interventricular septum skeleton. However, standard skeletonization algorithms suffer from multiple branches because the septum boundaries are not smooth. The IVST algorithm employs an additional pruning step (step 720) to the standard skeletonization algorithm to retain only the longest branch of the skeleton. The pruning step eliminates the multiple branches.

At step 730, the IVST algorithm divides the medial axis into multiple regions. The multiple regions may comprise any number n such as for example, n=10. Subsequently, at step 740, the IVST algorithm fits line segments into each of these n regions using linear regression. At step 750, n line segments are fitted to the n regions of the medial axis. Each of the line segments are defined as:

$$y = X\beta + \epsilon,$$

where X is a design matrix, β is a parameter vector, y is an observation matrix, and ϵ the least squares fit error. The least squares line parameters are given by:

$$\beta = (X^T X)^{-1} X^T y.$$

At step 760, the IVST algorithm identifies a projection line passing through the localized mitral valve tip for example, the mitral valve tip 620 of FIG. 6c with the smallest distance to each of the n line segments. Each of these projection lines are orthogonal to the respective line segment by virtue of being the smallest distance. Subsequently, at step 770, the shortest among the projection lines between the n line segments and mitral valve is selected as a measurement line. The IVST algorithm uses the following computation to select the measurement line:

Assume that $p_i$ is the point of intersection between the projection line and the respective line segment, $p_s$ is the starting point of the projection line, $p_e$ is the ending point of the projection line, $p_m$ is the point, where the projection line passes through the mitral valve and t is the distance from $p_i$ to $p_s$. The intersection location $p_i$ of the point $p_m$ with the line $\overline{p_s p_e}$ is calculated using the following functions:

$$t = -\frac{(p_s - p_m) \cdot (p_e - p_s)}{\|p_e - p_s\|^2}$$

where, t lies between [0,1].

$$p_i = p_s + t^*(p_e - p_s)$$

Using the processing equations, the Euclidean distance between point $p_i$ and point $p_m$ is calculated. Such computation is repeated for all of the line segments of the interventricular septum region, and the projection line with smallest distance between $p_i$ and $p_s$ is selected as the measurement line.

At step 780, the two points of intersection between the interventricular septum mask and measurement line are determined. The point of intersection between the near septum boundary, similar to for example, the near septum boundary 410 of FIG. 4 and the measurement line is referred to herein as Point 1. The point of intersection between the far septum boundary, similar to for example, the far septum boundary 420 of FIG. 4 and the measurement line is referred to herein as Point 2. At step 790, the IVST algorithm calculates the thickness of IVSd as the distance between Point 1 and Point 2.

Figure 8A:
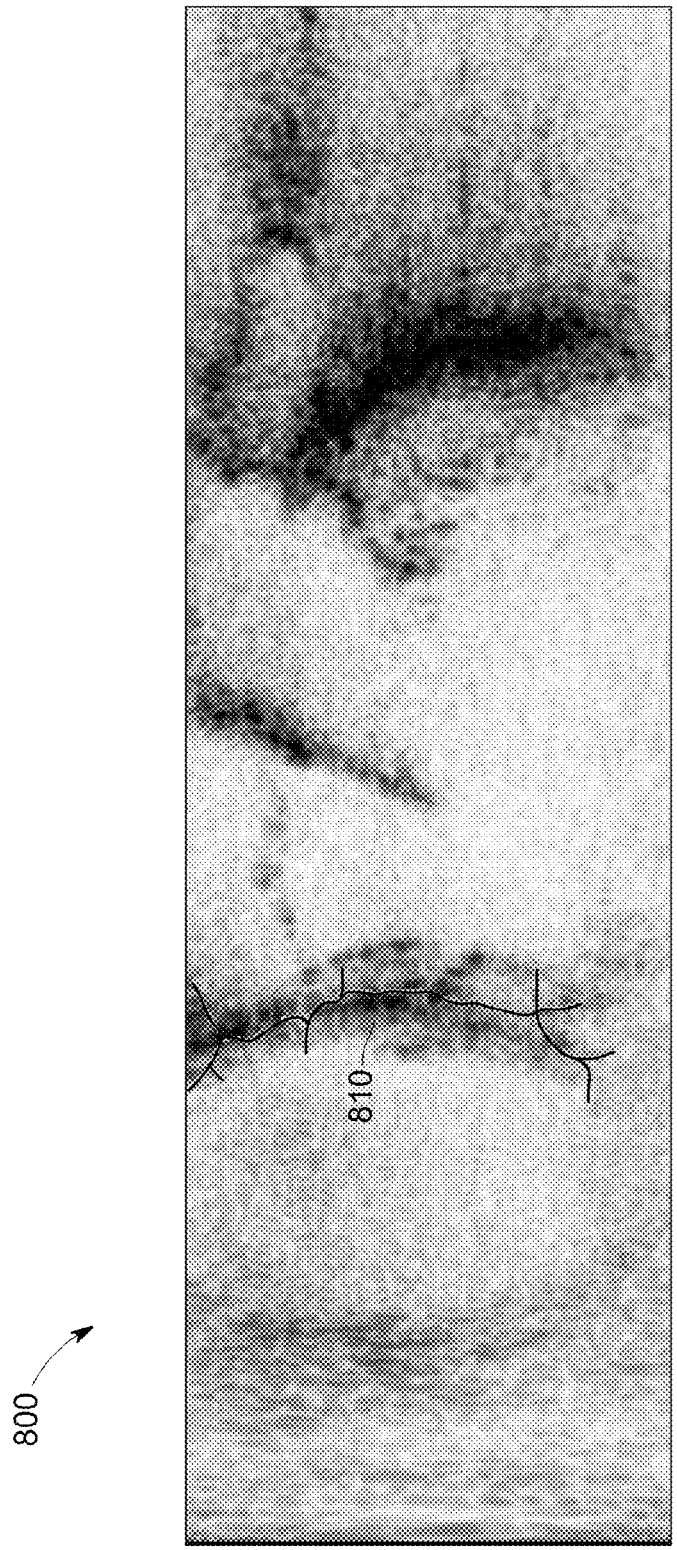
FIG. 8a is a part ultrasound image of the interventricular septum illustrating skeletonization of the interventricular septum, according to one embodiment.

FIG. 8a is a partial ultrasound image 800 of the interventricular septum illustrating skeletonization of the interventricular septum, according to an embodiment of the present disclosure. In the illustrated embodiment, the ultrasound image 800 represents the medial axis 810 of the interventricular septum calculated by the IVST algorithm for example, at step 710 of the method 700 with reference to FIG. 7.

Figure 8B:
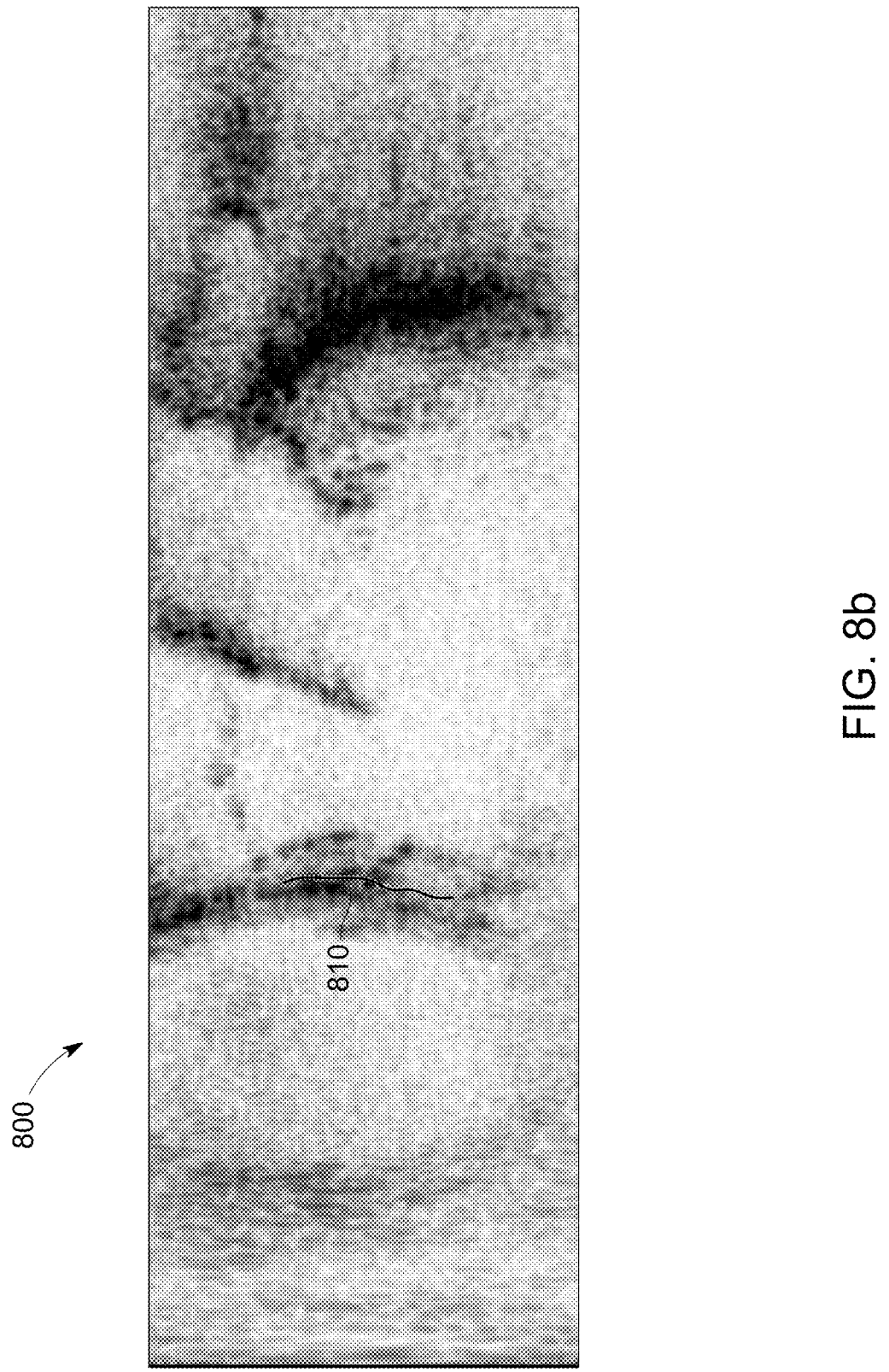
FIG. 8b is a part ultrasound image of the interventricular septum illustrating the pruned medial axis of the interventricular septum, according to a further embodiment.

FIG. 8b is a partial ultrasound image 800 of the interventricular septum illustrating the pruned medial axis of the interventricular septum, according to an embodiment of the present invention. In the illustrated embodiment, the ultrasound image 800 represents the medial axis 810 of the interventricular septum pruned by the IVST algorithm for example, at step 720 of the method 700 with reference to FIG. 7.

Figure 8C:
FIG. 8c is a part ultrasound image of the interventricular septum illustrating one of the n line segments fitted to the respective region of the medial axis, according to a further embodiment.

FIG. 8c is a partial ultrasound image 800 of the interventricular septum illustrating one of the n line segments 812 fitted to the respective region 822 of the medial axis 810, according to one embodiment. In the illustrated embodiment, the ultrasound image 800 represents the line segment 812 fitted to the region 822 of the medial axis for example, at step 750 of the method 700 with reference to FIG. 7. One example is to find the shortest projection line perpendicular to every point in the medial axis that passes through the mitral valve tip, but such a computation is highly memory intensive because there are many points in the medial axis. To make the method of measurement of the thickness of IVSd computationally tractable to allow for automation, the IVST algorithm uses the approach of dividing the medial axis into n regions and computing projection lines perpendicular to line segments that fit the n regions of the medial axis.

Figure 8D:
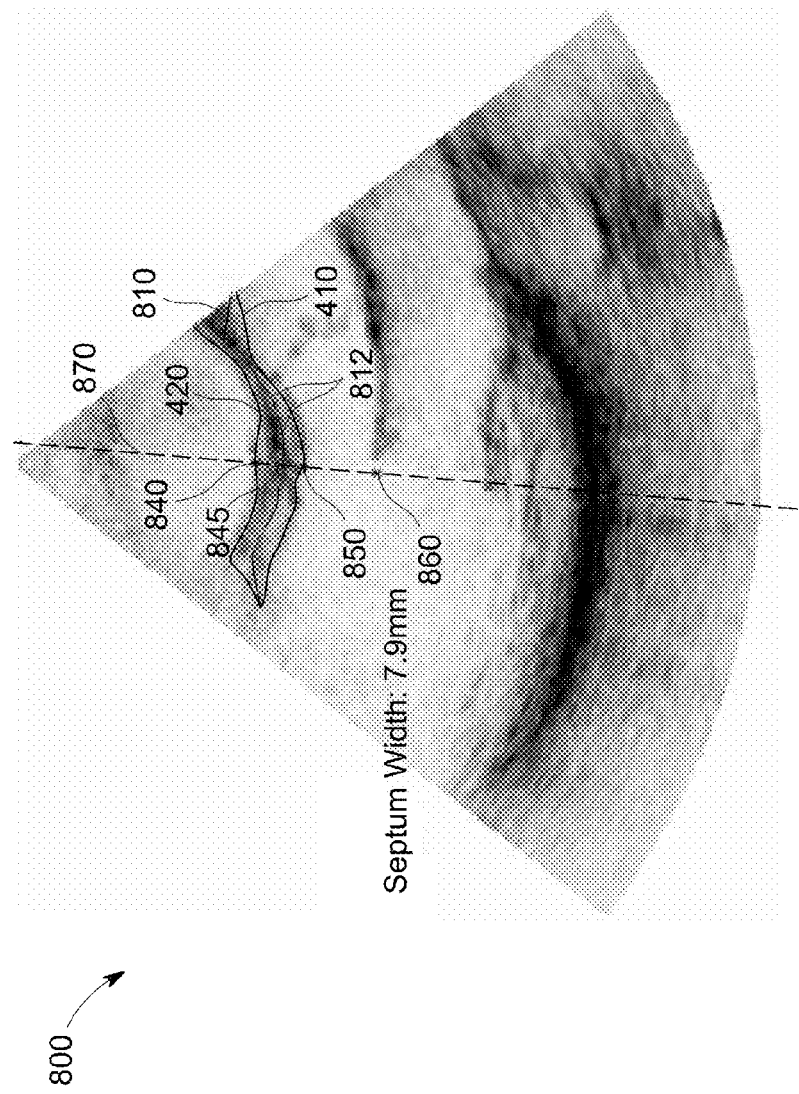
FIG. 8d is a PLAX view ultrasound image of the heart illustrating the method of automated measurement of interventricular septum thickness, according to a further embodiment.

FIG. 8d is a PLAX view ultrasound image 800 of the heart illustrating the method of automated measurement of the thickness of IVSd, according to an embodiment of the present disclosure. In the illustrated embodiment, the method of automated measurement of the thickness of IVSd comprises calculating the distance between the Point 1 850 and Point 2 840. The measurement line 870 is shown to be passing through the mitral valve tip at $p_m$ 860 and is orthogonal to the medial axis 410 at $p_i$ 845. The medial axis 810 comprises n line segments 812. The IVST algorithm calculates the thickness of the interventricular septum as the distance between Point 1 850 and Point 2 840, for example at step 790 of method 700 with reference to FIG. 7

Various embodiments (or equivalents thereof) discussed herein provide several advantages. For example, automating measurement of the thickness of IVSd eliminates the problem of inter- and intra-observer variability. The various embodiments discussed herein have a technical effect to provide a fully automatic real-time tracking of both anatomical structures, the mitral valve and the interventricular septum, required for measurement of the thickness of IVSd. Further, the localization of mitral valve tip using VTLA based on frame differencing approach provides a shorter running time. Frame differencing approach eliminates initializing or shape modeling limitations of conventional localization algorithms VTLA provides a robust solution for automatically localizing mitral valve tip in B-mode image sequences. For these reasons, the embodiments discussed herein achieve automatic measurement of the thickness of IVSd that offers benefits of reproducibility and time saving.

Unless defined otherwise, technical and scientific terms used herein have the same meaning as is commonly understood by one of skill in the art to which this invention belongs. The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation. If ranges are disclosed, the endpoints of all ranges directed to the same component or property are inclusive and independently combinable (e.g., ranges of "up to about 25 wt. %, or, more specifically, about 5 wt. % to about 20 wt. %," is inclusive of the endpoints and all intermediate values of the ranges of "about 5 wt. % to about 25 wt. %," etc.). The modifier "about" used in connection with a quantity is inclusive of the stated value and has the meaning dictated by the context (e.g., includes the degree of error associated with measurement of the particular quantity).

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for automated measuring of interventricular septum thickness, the method comprising:
   acquiring a series of ultrasound images of a heart;
   acquiring a septum mask by applying a septum segmentation algorithm on the series of ultrasound images;
   localizing a mitral valve tip using a valve tip localization algorithm, wherein the valve tip localization algorithm comprises;
      computing a motion map of a current frame of a sequence of the ultrasound images;
      identifying a set of candidate pixels comprising the motion map, the set of candidate pixels comprising a predetermined number of candidate pixels, wherein each of the candidate pixels corresponds to a location of high motion in the current frame;
      computing a location of a median for the set candidate pixels, the location of the median representing the mitral valve tip; and
   calculating the thickness of the interventricular septum using an interventricular septum thickness algorithm that uses the septum mask and the localized mitral valve tip as inputs.

2. The method of claim 1, wherein the interventricular septum thickness algorithm comprises:
   identification of a measurement line that is orthogonal to a medial axis of the interventricular septum and passes through the tip of the mitral valve; and
   calculation of a distance between a first point on the measurement line and a second point on the measurement line, the first point being a point of intersection of the measurement line and a near boundary of the interventricular septum, and the second point being a point of intersection of the measurement line and a far boundary of the interventricular septum.

3. The method of claim 2, wherein identification of the measurement line comprises:
   calculating the medial axis of the interventricular septum;
   dividing the medial axis into a plurality of regions;
   fitting line segments to each of the plurality of regions;
   identifying a line passing through the mitral valve tip with least distance to each of the plurality of line segments; and
   selecting the line that is the shortest as the measurement line.

4. The method of claim 3, wherein pruning is carried out to retain only a longest branch of the medial axis of the interventricular septum.

5. The method of claim 1, wherein septum segmentation algorithm is based on energy minimization and wherein energy further comprises local region intensity statistics and septum shape constraints.

6. The method of claim 5, wherein the septum shape constraints comprise smoothness and width constraints.

7. The method of claim 1, wherein the motion map of the current frame is computed based on the frame difference between the current frame and a previous frame.

8. The method of claim 1, wherein the motion map of the current frame is computed based on the frame difference between the current frame and a subsequent frame.

9. The method of claim 1, wherein identification of the plurality of candidate pixels is refined using region of interest as a constraint.

10. The method of claim 1, wherein the ultrasound image of the heart acquired comprises a parasternal long axis view.

11. An ultrasound apparatus for automated measurement of interventricular septum thickness, the apparatus comprising:
   a transducer array coupled to a transmit/receive processor that drives the transducer array to acquire a series of ultrasound images of a heart;
   a processing section coupled to the transmit/receive processor controlling and synchronizing functions of the ultrasound apparatus, said processing section comprises, a scan conversion module, a digital signal processing unit, a controller and a central processor;
   a memory device coupled to the processing section to store data used by the processing section;
   a program memory coupled to the processing section that stores software routines that are used by the controller;
   wherein the controller is coupled to the central processor, the digital signal processing unit, and the controller to control and synchronizes the processing and control functions of the ultrasound apparatus; and
   the central processor is configured to acquire a septum mask by applying a septum segmentation algorithm on the series of ultrasound images, the central processor configured to localize a mitral valve tip using a valve tip localization algorithm, wherein the valve tip localization algorithm comprises; computing a motion map of a current frame of a sequence of the ultrasound images
      identifying a set of candidate pixels comprising the motion map, the set of candidate pixels comprising a predetermined number of candidate pixels, wherein each of the candidate pixels corresponds to a location of high motion in the current frame;
      computing a location of a median for the set candidate pixels, the location of the median representing the mitral valve tip; and wherein the processor is further configured to calculate the thickness of the interventricular septum using an interventricular septum thickness algorithm that uses the septum mask and the localized mitral tip valve as inputs.

12. The ultrasound apparatus of claim 11, wherein the ultrasound imaging apparatus is configured as a hand-held device.

13. The ultrasound apparatus of claim 11, wherein the controller is also coupled to a user control to accept user inputs to controls operations of the ultrasound apparatus.

* * * * *